United States Patent [19]

Heinhuis-Walther et al.

[11] Patent Number: 5,000,867

[45] Date of Patent: Mar. 19, 1991

[54] DISINFECTANT COMPOSITIONS

[75] Inventors: Johanna M. C. Heinhuis-Walther, EP De Meern, Netherlands; Leonardus Lips, Emmerich, Fed. Rep. of Germany

[73] Assignee: Lever Brothers Company, New York, N.Y.

[21] Appl. No.: 496,065

[22] Filed: Mar. 16, 1990

Related U.S. Application Data

[63] Continuation of Ser. No. 333,856, Apr. 4, 1989, abandoned, which is a continuation of Ser. No. 109,341, Oct. 16, 1987, abandoned.

[30] Foreign Application Priority Data

Oct. 20, 1986 [GB] United Kingdom ............... 8625103

[51] Int. Cl.$^5$ .................... C11D 3/48; C11D 7/08; A61L 9/00
[52] U.S. Cl. .................... 252/106; 252/142; 252/547; 514/638; 514/642; 422/28
[58] Field of Search .............. 252/106, 142, 547; 514/638, 642; 422/28

[56] References Cited

U.S. PATENT DOCUMENTS

| | | | |
|---|---|---|---|
| 2,653,156 | 9/1953 | Deutsch et al. | 260/404 |
| 2,684,924 | 7/1954 | Rose | 514/635 |
| 2,990,425 | 6/1961 | Senior | 252/544 |
| 3,152,181 | 10/1964 | Shapiro et al. | 564/233 |
| 3,223,643 | 12/1965 | Law | 252/106 |
| 3,366,673 | 1/1968 | Wakeman et al. | 260/501.15 |
| 3,468,898 | 9/1969 | Cutler | 548/299 |
| 3,591,509 | 7/1971 | Parks et al. | 252/137 |
| 3,657,011 | 4/1972 | Orr | 134/17 |
| 3,855,140 | 5/1972 | Billany | 252/106 |
| 3,934,002 | 1/1976 | Haefele | 424/54 |
| 4,053,636 | 10/1977 | Eustis | 514/635 |
| 4,213,961 | 7/1980 | Curtis et al. | 424/54 |
| 4,256,731 | 3/1981 | Curtis | 424/54 |
| 4,294,852 | 10/1981 | Wildnauer | 514/635 |
| 4,304,591 | 12/1981 | Mueller et al. | 71/93 |
| 4,420,484 | 12/1983 | Gorman et al. | 424/326 |
| 4,612,135 | 9/1986 | Wenzel | 252/106 |
| 4,647,458 | 3/1987 | Ueno et al. | 424/128 |

FOREIGN PATENT DOCUMENTS

| | | |
|---|---|---|
| 004719 | 10/1979 | European Pat. Off. |
| 018492 | 11/1980 | European Pat. Off. |
| 131394 | 1/1985 | European Pat. Off. |
| 57-176903 | 10/1982 | Japan |
| 1239641 | 7/1971 | United Kingdom |
| 1296360 | 11/1972 | United Kingdom |
| 1344880 | 1/1974 | United Kingdom |
| 1431945 | 4/1976 | United Kingdom |
| 1551501 | 8/1979 | United Kingdom |
| 1569423 | 6/1980 | United Kingdom |
| 2074043 | 10/1981 | United Kingdom |
| 2133689 | 8/1984 | United Kingdom |

Primary Examiner—William R. Dixon, Jr.
Assistant Examiner—Helene Klemanski
Attorney, Agent, or Firm—Cushman, Darby & Cushman

[57] ABSTRACT

A sanitizing composition particularly suited to the cleaning-in-place of food industry equipment, comprises:
 (i) one or more quaternary ammonium anti-microbial agents and/or one or more substituted guanidine anti-microbial agents;
 (ii) one or more organic acids; and
 (iii) one or more inorganic acids.

10 Claims, No Drawings

DISINFECTANT COMPOSITIONS

This is a continuation of application Ser. No. 333,856, filed Apr. 4, 1989, now abandoned which is a continuation of application Ser. No. 109,341, filed Oct. 16, 1987, now abandoned.

The present invention relates to disinfectant compositions which are especially, but not exclusively, useful for the cleaning-in-place (CIP) of equipment used in the food industry.

A typical situation encountered in food industry CIP is the cleaning of the insides of dairy equipment such as that used in the ultra high temperature (UHT) treatment of milk where the apparatus is soiled by organic matter, mainly fat and protein, and inorganic deposits, mainly insoluble calcium salts such as the carbonate, phosphate and oxalate. Naturally, as well as removing both the organic and inorganic soiling, it is necessary to sanitize the equipment, i.e. to reduce the number of potentially harmful micro-organisms to an acceptable level.

To ensure that sanitization occurs, a composition for this purpose must contain at least one anti-microbial component. One class of anti-microbial substance comprises those of the quaternary ammonium type. For example, UK Patent Specification GB 1 239 641 describes disinfectant cleaning compositions including such a quaternary ammonium compound. These compositions also contain a hydroxycarboxylic acid and a detergent active (surfactant) agent. However, such compositions are not sufficiently effective in disinfection applications of the kind described in the preceding paragraph.

It has also previously been described that quaternary ammonium anti-microbials and/or those of the substituted guanidine type may be combined with acid components to provide disinfection of parts of the human body, for example in U.S. Pat. Nos. 4,420,484 and 4,213,961, in European Patent Specification EP 4,719 and UK Patent Specification GB 1,296,630. Since these components are intended to come into intimate contact with human tissue, they are not sufficiently aggressive to be efficacious in sanitization of hard surfaces encountered in the food industry.

We have now found that disinfection of surfaces in applications of the kind described above can be effected to a degree superior to that possible with existing market products by providing a sanitizing composition comprising:
  (i) a quaternary ammonium anti-microbial agent and/or a substituted guanidine anti-microbial agent;
  (ii) an organic acid; and
  (iii) an inorganic acid.

One surprising property of this composition derives from the fact that the microbial effect of quaternary ammonium anti-microbials in combination with inorganic acids is known to decrease with decreasing pH. However, we have found that incorporation of an organic acid significantly improves the fungicidal effect. We have observed this to be most marked with organic acids having from one to four carbon atoms, either with or without a hydroxyl group additional to that forming part of the carboxyl moiety. Examples of such organic acids are formic, lactic and citric acids. The organic acid can also be of a cyclic nature such as benzoic acid. However, whilst preferred, in the context of the invention in its widest sense, these specific organic acids are not to be considered limiting and further non-limiting examples of suitable organic acids are elaborated hereinbelow.

In general, of course the invention includes compositions containing more than one example of any of the ingredients defined in classes (i)-(iii) above. Within these classes, it is generally preferred that the total quantity quaternary ammonium anti-microbials (when present) should be from 0.01 to 50%, most preferably from 0.5 to 30%, especially from 1 to 25%. These percentages and unless the context requires otherwise, all others throughout this specification, are by weight. As a general guide, any one quaternary ammonium antimicrobial agent may be present from 0.5 to 15%, preferably from 1 to 12.5%.

Generally, the total quantity of substituted guanidine anti-microbials (when present) may be from 0.01 to 25%, preferably from 0.2 to 15%, most preferably 2 to 12.5%. The amount of any single substituted guanidine anti-microbial agent may for example be from 0.2 to 12.5%, preferably from 2 to 10%.

Generally, the total quantity of organic acids present may be from 0.1 to 75%, preferably from 0.5 to 50%, especially from 5 to 35%. The total amount of any single organic acid may for example be from 0.2 to 20%, preferably from 1 to 12.5%.

Generally, the total quantity of inorganic acids present may be from 1 to 99%, preferably from 10 to 95%, most preferably from 20 to 55%. The total amount of any single inorganic acid may for example be from 0.5-60%, preferably 2.5-45%.

The quaternary ammonium anti-microbial agent (if present) may be of any of such agents known to those skilled in the art, for example in W. Gump, Disinfectants and Antiseptics, Vol. 7, in "Encycl. Chem. Technol.", Kirk-Othmer Eds., 3rd Edn., pp 793-832, in the Patent literature references quoted above or in any of patent specifications EP 131,394, EP 110,568, GB 2,133,689, GB 2,074,043, GB 1,155,501, and U.S. Pat. No. 4,256,731.

The substituted guanidine anti-microbial agent (if present) also may be any known to those skilled in the art, for example any described generically or specifically in the patent literature references above or in German Patent Specification DE 2,332,383, UK Patent Specification GB 1,431,945 or in any of U.S. Pat. Nos. 3,934,002; 2,684,924; 4,053,636; 2,990,425; 3,468,898; 3,855,140 and 4,622,834.

Preferred compositions according to the present invention comprise both a quaternary ammonium and substituted guanidine anti-microbial agent.

More especially, the substituted guanidine agent may be a biguanide. In general, such a biguanide agent may be a monomeric or polymeric compound which includes one or more units of formula

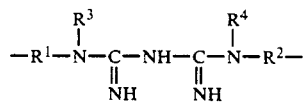

Where $R^1$-$R^4$ can be any of a variety of moieties. For example $R^1$ and $R^2$ independently may be bonds or $C_{1-4}$ alkylene chains optionally substituted by a phenyl radical (which itself optionally may be substituted by one or more suitable substituents such as alkyl or alkoxy), and $R^3$ and $R^4$ independently may be hydrogen, $C_{1-12}$ alkyl or $C_{7-12}$ aralkyl, and $R^1$ with $R^3$, and independently, $R^2$ with $R^4$ may form cyclic moieties.

The substituted guanidine (including biguanide) agents include the acid addition salts thereof, which may or may not form due to the presence in the composition of the present invention, of the organic and the inorganic acid.

One preferred biguanide is that sold by ICI under the Tradename "Vantocil IB".

As stated, the organic acid is believed to be necessary to enhance the anti-microbial properties of the composition. Although some preferred examples are recited above, in general such organic acids include those containing one or more carboxylic, hydroxycarboxylic or sulphonic acid groups. As well as those mentioned previously, examples of suitable organic acids are acetic acid, salycilic acid and hydroxybenzoic acid derivative anti-microbials such as are described in W. Gump supra.

The inorganic acid is preferably a strong mineral acid such as sulphuric, hydrochloric, nitric, orthophosphoric (otherwise known as "phosphoric"), boric or perboric acid. Of these, phosphoric acid is especially preferred.

Experimental results have demonstrated the unexpected phenomenon that compositions of the present invention which comprise both phosphoric and sulphuric acids are especially efficacious in removing not only calcium oxalate deposits, but also protein soiling. This effect is most marked when the phosphoric acid is present in the range 25-35%, preferably 5-25% by weight and the sulphuric acid in the range 2.5-25%, preferably around 30% by weight.

Compositions according to the present invention may also comprise one or more accessory ingredients.

Thus, although the composition comprising only components (i)-(iii) has some inherent ability to remove fatty organic soil, its action can be enhanced by incorporation of one or more detergent active (surfactant) agents. These are well known in the art and may in general, be selected from non-ionic, cationic, zwitterionic and amphoteric agents. Those of the non-ionic kind are preferred.

Examples of the detergent active (surfactant) materials which can be used for these compositions are described in detail in "Surface Active Agents and Detergents", Volumes I and II by Schwartz, Perry and Berch. In general, when such materials are present, their total presence may amount to from 0.01 to 25%, preferably from 0.1 to 5%, especially from 1 to 2.5%. As a rule, the total amount of any one such active may be from 0.1 to 3%, preferably from 1 to 2%.

Other optional ingredients include solvents, hydrotropes, thickeners, abrasives and other anti-microbial agents. In general, the remainder of any such composition may comprise water. To ensure optimum removal of inorganic soil, it is preferred that compositions according to the invention have a pH of 5 or less, especially 4 or less and most preferably, less than 4.

Of these ingredients, hydrotropes (when present) in total may for example be included at from 0.01 to 25% by weight, preferably from 0.2 to 15%, especially from 1 to 7.5%. In general, any one hydrotrope may be present at from 0.1 to 10%, preferably 1 to 5%.

Thickeners (when present) in total may for example be included at from 0.01 to 10% by weight, preferably from 0.02 to 5%, especially from 0.2 to 2.5%. As a rule, any one hydrotrope may be present at from 0.05 to 30% by weight, preferably from 0.5 to 20%, especially from 1 to 15%.

Other (non-quaternary and other than substituted guanidine) anti-microbials which may be included are sodium benzoate, as well as those of the amine oxide and dioxide kind. Generally, it is preferred to include both sodium benzoate and an amine oxide. As a rule, such other anti-microbials (when present) may be included at from 0.1 to 40% by weight, preferably from 0.5 to 20%, most preferably from 1 to 15%. Normally, any one such other anti-microbial may be present at from 0.1 to 15%, preferably from 0.2 to 10%.

The compositions of the present invention may be applied to any suitable surface it is desired to cleanse but they are especially suitable for equipment CIP. It is preferred that they be applied in diluted form. Generally, this dilution may be at from 0.05 to 10% in aqueous medium but especially from 0.2 to 2%. The appropriate working concentration or concentration range will of course vary according to the amount of each ingredient in the undiluted composition. These values can be determined by suitable tests (for example as referred to herein) which will readily be apparent to those skilled in the art of formulating disinfectants.

In most situations, the cleansing step requires leaving the composition in contact with the surface for a suitable period of time, followed by rinsing with water. Within the CIP area, applications in the food industry are eminently suitable, for example in dairies and breweries. Thus, as well as the UHT equipment cleaning referred to above, another application is in the cleaning of bright beer tanks in the brewing industry. (In the context of the present invention, "cleansing" and "cleaning" include sanitisation/disinfection but not necessarily to the degree of killing substantially all microorganisms present).

The present invention will now be further elaborated by way of the following non-limiting Examples.

EXAMPLES

Examples 1-7 are sanitizing compositions made-up according to the following table (quantities are % by weight):

| EXAMPLE | 1 | 2 | 3 | 4 | 5 | 6 | 7 |
| --- | --- | --- | --- | --- | --- | --- | --- |
| Phosphoric Acid (85%) | 40.0 | 40.0 | 40.0 | 40.0 | 40.0 | 40.0 | 40.0 |
| Plurafac RA30 | 1.5 | — | 1.5 | — | — | 1.5 | 1.5 |
| Sulphuric Acid (95%) | — | — | — | 3.0 | — | — | — |
| Formic Acid (85%) | 11.8 | — | 11.8 | 5.9 | 11.8 | 11.8 | — |
| Empigen OB (30%) | — | 3.3 | — | 3.3 | 3.3 | — | — |
| Sodium Benzoate | — | — | — | 8.3 | — | — | — |
| Bardac 22 | 10.0 | — | 10.0 | — | 10.0 | 10.0 | 10.0 |
| Bardac LF | — | 12.0 | — | — | — | — | — |
| Dodigen 226 (50%) | — | 12.0 | — | — | — | — | — |
| Vantocil IB (20%) | 10.0 | — | — | — | — | — | — |
| Citric Acid | — | — | — | — | — | 2.0 | — |
| Lactic Acid | — | — | — | — | — | — | 12.0 |
| Butyldioxitol | 2.5 | — | — | — | — | — | — |
| Jaquat C13 | — | — | — | 0.5 | — | — | — |

EXAMPLE-continued

|  | 1 | 2 | 3 | 4 | 5 | 6 | 7 |
|---|---|---|---|---|---|---|---|
| Water |  | 24.2 | 32.7 | 36.7 | 39.0 | 34.9 | 34.7 | 36.5 |

Notes:
Plurafac RA30 is a nonionic surfactant.
Empigen OB is a 30% active solution of (70% $C_{11}$, 30% C13 average) dimethyl amine oxide (anti-microbial) ex Albright and Wilson.
Bardac 22 is 50% active didecyl dimethyl (quaternary) ammonium chloride, a cationic surfactant, ex Lonza Inc.
Bardac LF is 50% active dioctyl dimethyl (quaternary) ammonium chloride, a low foaming cationic surfactant, ex Lonza Inc.
Dodigen 226 is an alkyl benzyl type quaternary ammonium agent.
Vantocil IB is as hereinbefore defined.
Butyldioxitol is a hydrotrope.
Jaquat C13 is a proprietory thickener.

TEST RESULTS

The compositions of Examples 1-7 were tested in various aqueous concentrations in a standard suspension test for reduction of numbers of *Saccharomyces cerevisiae* at 4° C. (method as described in B van Klingeren, "Two-Tier Test System for the Evaluation of Disinfectants", Ph.D. Thesis, University of Utrecht, except using *S. cerevisiae* instead of *Candida albicans*).

Results are presented as the minimum use concentration of composition which demonstrated a log decimal reduction (LDR) greater than 4.0.

| Example | % |
|---|---|
| 1 | 0.5 |
| 2 | 1.0 |
| 3 | 0.5 |
| 4 | 1.0 |
| 5 | 1.0 |
| 6 | 0.25 |
| 7 | 0.25 |

EXAMPLES 8 and 9

Other forms of composition according to the invention, particularly suited to open plant cleaning is set forth below. Quantities are in % by weight and the intended applied concentration is from 4-10%.

| Ex. 8: | Water | 47.5 |
|---|---|---|
|  | Phosphoric acid | 30.0 |
|  | Alkyl benzene sulphonic acid | 8.0 |
|  | Diethylene glycol mono-n-butyl ether | 10.0 |
|  | Organic acid (formic/lactic) | 2.0 |
|  | Citric acid | 0.5 |
|  | C10 lin. alkyl quaternary ammonium compound | 2.0 |

| Ex. 9: | Lactic acid (80%) | 12 |
|---|---|---|
|  | Citric acid (1 aq.) | 4 |
|  | $H_3PO_4$ (85%) | 30 |
|  | $H_2SO_4$ | 5 |
|  | Foam depressor (Hoechst KN) | 2 |
|  | Surfactant: Lutensol LF 431 | 2 |
|  | Lin. quat. (Bardac 22-50%) | 10 |
|  | Water | 35 |

We claim:

1. A sanitising composition comprising:
   (i) one or more quaternary ammonium anti-microbial agents, the total quantity of quaternary ammonium anti-microbial agents being 0.01 to 50%;
   (ii) one or more organic acids selected from the group consisting of formic, lactic and citric acid, the total quantity of organic acid being 0.1 to 75%;
   (iii) 0.5 to 60% phosphoric acid; and
   (iv) one or more substituted guanidine anti-microbial agents, the total quantity of guanidine agents being 0.01 to 25%.

2. The sanitising composition according to claim 1 further comprising sulphuric acid in an amount of 0.5 to 60%, the total amount of phosphoric and sulphuric acids being 1 to 99%.

3. A composition according to claim 2, wherein when present, the total quantity of quaternary ammonium anti-microbial agent(s) is from 0.5 to 30% by weight;
   when present, the total quantity of substituted guanidine anti-microbial agent(s) is from 0.2 to 15% by weight;
   the total quantity of organic acids is from 0.5 to 50% by weight; and
   the total quantity of phosphoric and sulphuric acid is from 20 to 55% by weight.

4. A composition according to claim 1 comprising a substituted guanidine anti-microbial agent which is a polymeric biguanide.

5. A composition according to claim 1 further comprising a surfactant.

6. A composition according to claim 5, wherein the surfactant is a non-ionic material.

7. A composition according to claim 1, further comprising sodium benzoate and an amine oxide anti-microbial.

8. A method of sanitising a surface, comprising applying to said surface, a composition according to claim 2.

9. A method according to claim 8, wherein said composition is applied at from 0.05 to 10% in aqueous dilution.

10. A method according to claim 9, wherein the composition is applied at from 0.2 to 2% in aqueous dilution, said composition having a total quantity of quaternary ammonium anti-microbial agent(s) being from 0.1 to 50% by weight;
   the total quantity of substituted guanidine anti-microbial agent(s) is from 0.01 to 25% by weight;
   the total quantity of organic acid(s) being from 0.01 to 75% by weight; and
   the total quantity of phosphoric and sulphuric acid present being from 1 to 99% by weight.

* * * * *